United States Patent
Lex

[19]
[11] Patent Number: 5,923,434
[45] Date of Patent: Jul. 13, 1999

[54] SURFACE QUALITY AND COLOR MEASURING DEVICE

[75] Inventor: Konrad Lex, Königsdorf, Germany

[73] Assignee: BYK-Gardner GmbH, Germany

[21] Appl. No.: 08/809,508

[22] PCT Filed: Sep. 24, 1995

[86] PCT No.: PCT/EP95/03788

§ 371 Date: Jul. 31, 1997

§ 102(e) Date: Jul. 31, 1997

[87] PCT Pub. No.: WO96/09531

PCT Pub. Date: Mar. 28, 1996

[30] Foreign Application Priority Data

Sep. 24, 1994 [DE] Germany ............... 44 34 203

[51] Int. Cl.⁶ ............... G01N 21/55; G01B 11/30
[52] U.S. Cl. ............... 356/445; 356/371
[58] Field of Search ............... 356/445–448, 356/371, 405–407; 250/226

[56] References Cited

U.S. PATENT DOCUMENTS 4,750,140  6/1988  Asano et al. .

FOREIGN PATENT DOCUMENTS

| 0 519 409 | 12/1992 | European Pat. Off. . |
| 42 29 349 | 3/1994 | Germany . |
| 4-72551 | 3/1992 | Japan . |
| WO 94/23283 | 10/1994 | WIPO . |

*Primary Examiner*—Robert Kim
*Assistant Examiner*—Amanda Merlino
*Attorney, Agent, or Firm*—Ohlandt, Greeley, Ruggiero & Perle

[57] ABSTRACT

A device for measuring the visual characteristics of surfaces comprises a light source the light of which is directed onto the measurement surface under a predetermined angle, and a measurement means which measures the light reflected from said measurement surface, said measurement means comprising at least three photo sensors which are arranged such that they measure the intensity of the reflected light in sections which correspond to a different reflection angle. The photo sensors form an integrated device, a common substrate being provided on which the light sensitive sources are arranged in essentially one plane and detect the amount of incident light essentially independently of each other, said light sensitive layers being designed such that they detect the amount of light reflected in a predetermined angle range each.

44 Claims, 6 Drawing Sheets

SURFACE QUALITY AND COLOR MEASURING DEVICE

This invention relates to a device for measuring the visual characteristics of surfaces.

As "visual characteristics" of a surface the physical characteristics of a surface which determine the appearance of this surface to the human observer, i. e. more specifically characteristics such as color, gloss, surface textures and the like, are here to be understood.

BACKGROUND OF THE INVENTION

A device for measuring visual characteristics of surfaces and, more specifically, the reflection behavior of surfaces, has been disclosed in EP-B-0 438 468. In this known device, a light source is provided, the light of which is directed onto the surface to be measured under a predetermined angle. The light reflected from said surface under a corresponding angle is measured by a light-sensitive sensor. Thus, it is possible to detect the gloss of the surface. The known device is used to judge the gloss behavior of vehicle paintures and the like, for example.

The function of this device will be described in the following with respect to the gloss measurement:

Using this known device, only a statement about the gloss behavior of surfaces in the area is possible, where the Fresnel reflection law is valid, i. e. the angle of reflection equals the angle of incidence. Actually a diffuse reflection is superimposed on this so-called mirror reflection, said diffuse reflection leading to an appearance of said surface which is referred to as haze. For glossy surfaces having haze the contrast and the brilliance of the reflection is diminished, whereby the surface provides a high gloss value from the point of the measurement, but from the point of the human observer it is no longer judged as clear but as milky or turbid.

Figure 11:
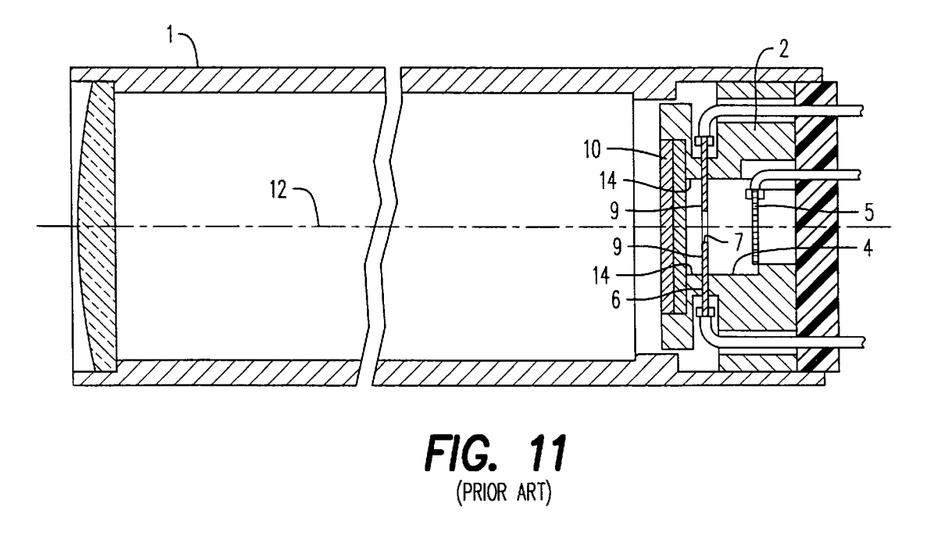
FIG. 11 is a conventional device for measuring gloss and haze.

For the measurement of haze usually a device is used as depicted in FIG. 11. This known device comprises a tubus 1 in which a body 2 is incorporated. In this body 2 a slit 4 is provided, the lower end of which is terminated by means of a photo cell 5.

The slit 4 is covered by a plate 6, in the middle of which an aperture 7 is provided and on which a photo sensor 9 is arranged, respectively. Above said photo sensor a usual filter unit 10 is provided.

By means of this apparatus it is possible to measure a gloss value and values of the haze. At this time the angle deviation which occurs between the ideal reflection angle for exact Fresnel reflection and the angle in which the light quantity is detected by the haze sensors, amounts to approximately 2°.

The function of this usual device is as follows: The surface to be measured is illuminated by a not illustrated light source, and an optic is provided to guide the reflected light into the tubus illustrated in FIG. 10. In this case the direction of the incidence of light exactly runs in parallel to the longitudinal axis 12 of the tubus. The light which is straightly reflected into the direction of the angle of reflection passes through the slit 7, which is the gloss aperture, onto the photo sensor 5. The intensity of the incident light quantity is a measure of the reflection capability of the surface and thus for its gloss.

The light which is reflected from the surface under a slightly smaller or larger angle, does not impinge onto the gloss aperture 7, but impinges partly onto the photo sensors 9. Their area is limited by edges 14 and by the slit 7 of the gloss aperture.

The intensity of the light impinging onto the sensors 9 is a measure of the haze. For an exactly reflecting surface, for example a mirror, the total reflected amount of light passes through the slit 7 onto the photo sensor 5, and no light impinges onto the photo sensors 9. For a highly brilliant surface exhibiting haze, however, a larger amount of the light impinges onto the sensors 9.

This known apparatus exhibits the disadvantage that the manufacturing accuracy has to be high in order to obtain meaningful measurement results. In this respect, especially the gloss aperture and the edges 14 which limit the impinging area of the photo sensors at the sides, have to be very accurately manufactured. Particular difficulties arise if the apparatus should be manufactured with small size, for example to be applied as a manual apparatus in the production supervision or the like. In this case the dimensions of the aperture is decreased and the manufacturing efforts are correspondingly enhanced.

SUMMARY OF THE INVENTION

It is an object of the present invention to provide a device for measuring visual characteristics of surfaces which involves a reduced manufacturing effort in comparison to the state of the art and which is substantially smaller constructed than devices known in the state of the art.

Another aspect of this object is providing a device for measuring visual characteristics for which despite of the compact construction in accordance with the first aspect of the object of the invention the possibilities of measuring are substantially improved in comparison to the state of the art of known devices. Another aspect of the object of the invention is providing a method which enables an advantageous detection of the visual characteristics of surfaces.

Accordingly, the present invention provides a method and device for achieving the above objects.

In the inventive apparatus the sensors are arranged in a common plane in contrast to the conventional device. The photo sensors define light-sensitive areas on a common substrate, the area of each light sensitive layer being selected such that it corresponds to a predetermined angle range of the reflection angle in the measurement device.

In the inventive device the up to date required apertures so as to guide the light rays onto the respective photo sensor to be used may be omitted. The light sensitive layers of the photo sensors themselves replace the apertures.

In the manufacture of these light sensitive layers commonly known techniques for manufacturing semiconductor devices and integrated circuits may be used enabling the light sensitive layers to be arranged on the common substrate with highest precision with respect to the areal expansion. By application of these techniques it is also possible to make small the distance which the light sensitive areas exhibit with respect to each other in order to be electrically isolated from each other.

By this construction it is possible to make the light sensitive areas relatively small. Thereby the distance from the measuring surface may be decreased so as to manufacture the apparatus with small size as a whole.

Although for the above described conventional apparatus the length of the measuring head amounts to 30 cm, it is possible to reduce the dimensions to value in the range of 5 to 10 cm with the inventive design, i. e. the size reduces to ¼ of that of the conventional measuring device.

Moreover the mechanical manufacturing and the installation and the adjustment of the apertures may be omitted such that the effort for the design of the device as a whole is substantially diminished. Moreover the device becomes also more robust by omitting the mechanical elements such that the application in the production involves substantially less problems than for the devices known so far.

The photo sensors may be designed differently. Preferably substrate and light sensitive layer are selected such that the photo sensors act as a photo diode. It is also possible to design the photo sensors as photo transistors or photo thyristors or the like.

In order to measure gloss and haze, preferably three light sensitive areas are used, the intermediate area being arranged for gloss measurement and at the left and at the right of this area a correspondingly designed area being arranged for the detection of the haze. The areas are selected such that the angle distance from the center of the measuring device, i. e. from a plane of symmetry of the light sensitive layer for gloss measurement, to the plane of symmetry of the haze measurement amounts to 1.8±0.3°. Of course, also different embodiments are possible.

The arrangement of two light sensitive areas in an angle distance of 2° with respect to the ideal angle of incidence, i. e. with respect to the angle of incidence in accordance to the reflection law, is very advantageous to judge the phenomena of haze. Besides an angle distance of 2° there are further angle distances, however, which have gained importance for the judgment of reflection characteristics of surfaces.

Also in the American standard ASTM E 430 a measurement angle of 0.3° is standard besides the measurement angle of 2°, being suited for the detection of a reflection characteristic which is referred to as distinctness of image (shortly D/I).

The light sensitive surface for the D/I measurement is arranged between the light sensitive area for the particular gloss measurement (ideal angle of incidence) and the light measuring area of 2°.

Another judgment criteria according to the ASTM standard for the reflection characteristics of surfaces is the reflection in an angle of 5° with respect to the ideal reflection angle. In another preferred embodiment of the invention also in this angle position a light sensitive area may be provided so as to detect the amount of light reflected into this range. It is preferable that also this light sensitive area or for a symmetrical arrangement these light sensitive areas are arranged on the same substrate as the surfaces for D/I and for haze measurement. It is also possible that in this case these areas are arranged in the same plane, however, on a separate substrate.

Reflection measurements are usually performed such that the incident light ray and the reflected light ray lie within the same plane. This is achieved if both light rays are in the same plane which is exactly perpendicular to the measuring surface.

Specifically for a simplified construction of the device it is conceivable that the requirement of an exactly perpendicular impinging of the light onto the measuring surface is not achieved. In this case it is preferable that plural light sensitive areas with respect to the impinging plane of the light ray onto the surface are arranged side by side. In this embodiment by comparison of the measurement values of the single areas the main reflection direction of the surface can be determined.

In another preferred embodiment of the invention a plurality of light sensitive areas are arranged in a plane field on a common substrate. In this case all field elements preferably exhibit the same dimensions.

In this embodiment a control means is also provided which exhibits a memory to store predetermined measurement field geometries. If such a sensor element is used for performing a reflection measurement, these light sensitive areas are used for the measurement which lie in the respective geometrically defined measurement range. Thus it is possible to change the measurement range arbitrarily and to imitate the measurement behavior of different reflection measurement apparatus.

For the reflection measurement the exposure of the surface to be measured is usually provided such that the light rays coming from the light source are directed in parallel under a predetermined angle to the surface. Such a light source having parallel light rays can be advantageously used in all embodiments described above.

Alternatively, in all embodiments described above a light source having a point-like characteristic may be used. For such a point light source the rays do not impinge in parallel onto the surface to be measured but under mutually different angles. When using such a point light source it is possible to perform measurements and judgments of visual characteristics of surfaces which are not possible using parallel light rays.

In a preferred embodiment of all construction examples given above it is possible to arrange a light source thus that optionally an exposure of the surface to be measured using parallel light rays or using a point light source is possible. For example, this can be achieved by removing the lens arrangement through which the light source irradiates the surface in order to obtain a parallel ray arrangement, out of the ray path. Moreover, it is conceivable that in the same apparatus two different measurement arrangements, for example having two different measurement angles are accommodated.

For all embodiments described so far it is assumed that the light sensitive areas are provided to detect the intensity of the light impinging thereon. Particularly, however not exclusively for the embodiment in which a plurality of light sensitive areas is used, it is preferable to arrange the light sensitive areas such that they exhibit a different spectral characteristic such that not only the intensity but also the spectral characteristic and, if the spectral characteristics of the light sensitive areas are correspondingly selected, also the color of the light reflected from the surface can be determined.

Apparatively, this last described alternative can be realized in a compact construction by using a color CCD chip for measuring the reflected light. In such a case the device can also be directly applied for a color measurement. In order to adapt the device to the different valid standards for color measurements in this case it is preferable that a light source is used which irradiates onto the surface to be measured under such an angle that the reflection parts essentially associated to a Fresnel reflection are not detected by the sensor.

Further advantages, features and applications of the present invention will become apparent from the following description of embodiments with respect to the accompanying drawings, wherein:

DESCRIPTION OF THE PREFERRED EMBODIMENTS

A first embodiment of the invention will now be described with reference to FIG. 1.

Figure 1:
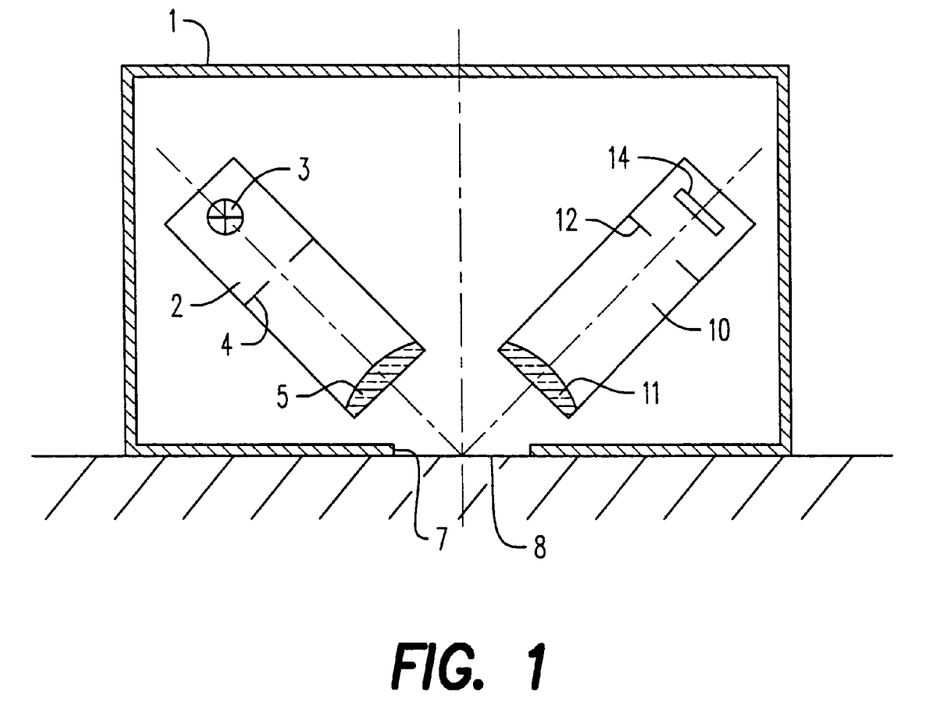
FIG. 1 is an embodiment of the present invention.

The reflection measurement device of FIG. 1 exhibits a housing 1 in which a first illumination tubus 2 is arranged. In this illumination tubus a light source 3, an aperture 4 and a lens 5 are arranged, as schematically indicated.

By means of the lens 5 it is achieved that the light impinges onto the measurement surface 8 in parallel and focused by the aperture 7. From the measurement surface the light is reflected and enters into the measurement tubus 10. This measurement tubus also includes a lens 11 as well as an aperture 12 and behind said aperture 12 the actual sensor 13.

The reflection measurement device further comprises a control means (not illustrated) by which the operation of the device is controlled, and also a display means (also not illustrated) by which the measured reflection values may be displayed.

The construction of the measurement sensor 14 will now be described with reference to FIG. 2 and FIG. 3.

In a common substrate 20 four metal pins 21, 22, 23, 24 serving as electrical connectors are arranged, the connector 22 being the common anode.

On this common substrate three light sensitive areas as layers being electrically separated from each other are arranged, namely a first light sensitive area 25 and a respective symmetrically arranged light sensitive area 26 and 27. The light sensitive area 25 is rectangular, the symmetry lines of the rectangle coinciding with the symmetry lines of the circular substrate and of the electrical connectors.

The light sensitive areas 26 and 27 are also rectangularly designed and approximately correspond to the width of the light sensitive area 25 regarding their width dimension, whereas the length dimension is slightly larger than the length dimension of the light sensitive area 25. The light sensitive areas are connected with the respective electrical connector 22, 23, 24.

In this embodiment the width of the light sensitive areas amounts to approximately 0.8 mm, the length of the area 25 amounts to approximately 1.5, and the length of the areas 26 and 27 amount to approximately 2.4 mm. These values are only referred to as an example and are not limitation of the dimension neither in the upward direction nor in the downward direction.

The substrate as well as the material and the construction of the light sensitive areas 25, 26 and 27 are selected such that each of these areas constitutes the light sensitive area of a sensor diode.

The control means activates the light source 3 the light of which impinges onto the measurement surface 8 having parallel rays. From the measurement surface 8 the light is reflected, passes through the lens 11 and through the aperture 12 and impinges onto the sensor 14. The sensor 14 is arranged such that a straight line the direction of which corresponds to the ideal angle of reflection exactly runs through the crossing of the symmetry lines of the measurement surface 25.

The light impinging onto the light sensitive layer 25 is measured by the control means and is a measure of gloss. In this case the determination of the gloss characteristic value is performed such as described in the EP-B-0 438 468.

If the measurement surface 8 is not an ideal reflecting mirror surface, light is also reflected into a direction which deviates from the ideal reflection angle. A part of this light impinges onto the light sensitive areas 26 and 27, such that a corresponding light current may be measured there. The corresponding electrical signal is a measure for the haze.

Since all light sensitive areas can be arranged very exactly on the substrate, it is possible to keep the areas relatively small as in the embodiment. In this case it is possible to make the distance between the measurement surface 8 and the sensor 14 very small, such that the device can be manufactured with very small size as a whole.

The embodiment of FIG. 1 is illustrated for an angle of 45°. Corresponding to the usual measurement geometries this angle may be changed, thus also angles of 20°, 30°, 45°, 60° and 85° are possible. If alternative standards are the basis of the reflection measurement, these values may also be arranged differently.

Moreover, in the embodiment of FIG. 1 a light tubus is provided which emits light under a predetermined angle with respect to the surface, and a tubus 14, in which the reflected light is measured. Instead also two or three corresponding devices may be integrated in one device as shown in the EP-B-0 438 468. If two or three corresponding devices are arranged, different measurement angles and measurement geometries may be used in the same device.

Furthermore, in the device of FIG. 1 the light ray is directly guided onto the surface. Especially for large reflection angles instead of directly guiding also deflection elements may be used, for example total reflecting prisms or light guides deflecting the light such that it impinges onto the surface under the desired measurement angle. If such a light deviating element is used, advantageously also the other side of the measurement device, i. e. the tubus having the sensor, is provided with corresponding deflecting elements.

Another embodiment of the invention will now be described with regard to FIG. 4. This embodiment is arranged as the one in FIG. 1 and may be equipped with corresponding light deflecting means as described with regard to FIG. 1. In contrast to the design of FIG. 1, however, the sensor 14 is differently arranged than illustrated in FIG. 2 and FIG. 3.

The sensor 14 comprises an essentially rectangular substrate 30 on which a plurality of light sensitive areas is arranged. In this case the intermediate area 31 corresponds to the light sensitive layer 25 in the embodiment in accordance with FIG. 2 and is arranged such that the ideal angle under which the light is reflected from the measurement surface crosses the crossing point of the symmetry lines of the rectangle 31.

Besides this light sensitive area 31 two narrow areas 32 and 33 are provided which serve to the above-mentioned D/I measurement.

Figure 2:
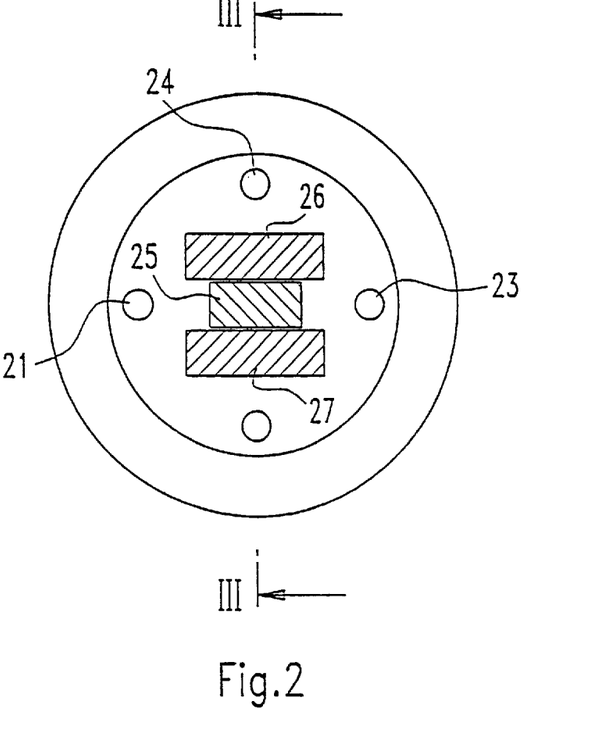
FIG. 2 is a view of the sensor element used in the device in FIG. 1.

Besides these fields 32, 33 also fields 34, 35 are provided which have the same function as the fields 26 and 27 in the embodiment of FIG. 2 and serve for the measurement of haze.

These fields essentially exhibit a distance of about 2° from the ideal reflection angle.

Adjacent to the fields 34 and 35 are light sensitive areas 36, 37 which in their magnitude correspond to the areas 34 and 35, however are arranged under an angle distance of 5° from the ideal reflection angle.

The operation of this device is the same as for the device of FIG. 1. In contrast to the device shown there, however, here different values which serve to the reflection judgment of the surface and are normalized in the cited ASTM E 430 for example may be measured. In this case the arrangement as also the arrangement of the embodiment of FIG. 2 is very simple and does not require a complicated aperture or slit arrangement as the conventional known apparatus.

Figure 4:
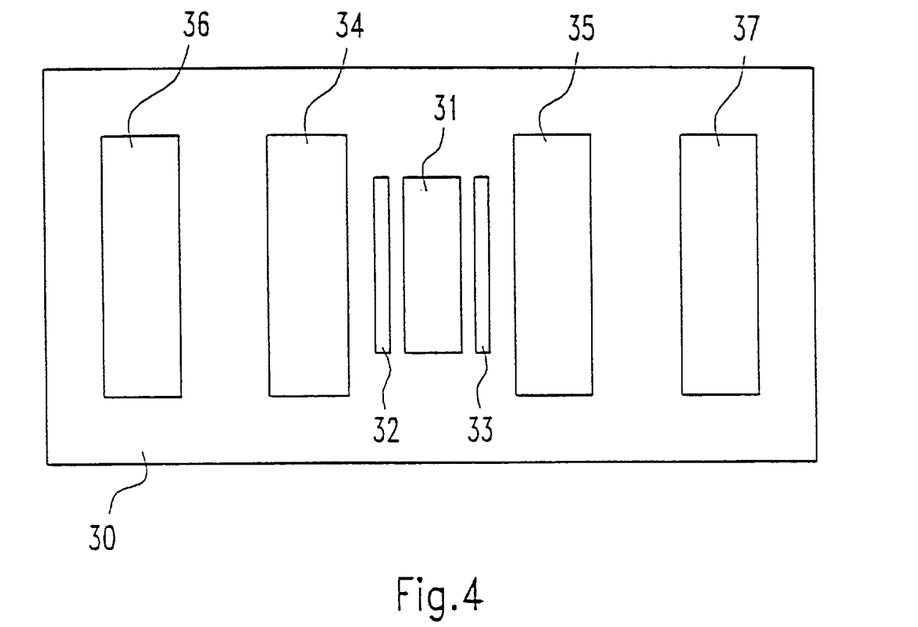
FIG. 4 is a view of another embodiment of a sensor element.

In the embodiment of FIG. 4 the distance between the outer fields 36, 37 and the adjacent fields 34, 35 is relatively large, the fields 34, 35 exhibiting an angle distance of 2°, whereas the fields 36, 37 exhibit an angle distance of 5° from the ideal reflection angle.

In this embodiment it is also possible to arrange the field 36, 37 on a dedicated substrate independent of the remaining fields, but also these fields being arranged in the same plane as the remaining fields.

Another embodiment of a sensor means that can be used in the device of FIG. 1 will now be described with respect to FIG. 5.

In this sensor means the same arrangement of the fields is shown as also depicted in FIG. 4. The reference signs are therefore identical and only marked with a prime for distinction.

The difference with respect to the design of FIG. 4 resides in the fact that the single fields 31'–37' are divided three times in their longitudinal direction, whereby field portions 31'$a$, 31'$b$ and 31'$c$, 33'$a$, 33'$b$, 33'$c$ and 37'$a$, 37'$b$, 37'$c$ are formed.

Figure 3:
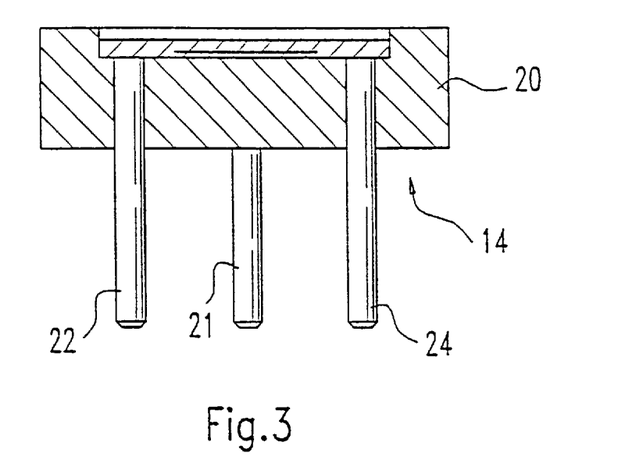
FIG. 3 is a cross section of the sensor element of FIG. 2.

Apart from one change, the operation of this device is the same as in the embodiment of FIG. 1 and FIGS. 2–3. The change resides in the fact that the (not illustrated) control means during the measurement compares the light intensities measured with the light sensitive areas 31'$a$, 31'$b$ and 31'$c$. The same is true for the remaining fields, i. e. the intensities which have been detected in the fields 35'$a$, 35'$b$ and 35'$c$ are similarly compared. By this comparison in the control means it is judged which of the field portions a, b and c has the highest intensity. For the further analysis of the measurement only these intensities are taken into account which have been measured in corresponding fields, namely in all fields having the letter a or in all fields having the letter b or in all fields having the letter c.

The advantage of this arrangement is that a displacement within the reflection plane can be recognized and corrected by the device. For an exactly oriented reflection plane the highest intensity will be measured in the fields b. If the reflection plane displaces because of inaccuracies of the measuring device itself, because of a not exact placing of the measurement device onto the measurement surface or because of a corresponding design of the measurement surface itself with respect to the ideal reflection plane, then this is recognized and taken into account by the device in the shown arrangement.

Figure 5:
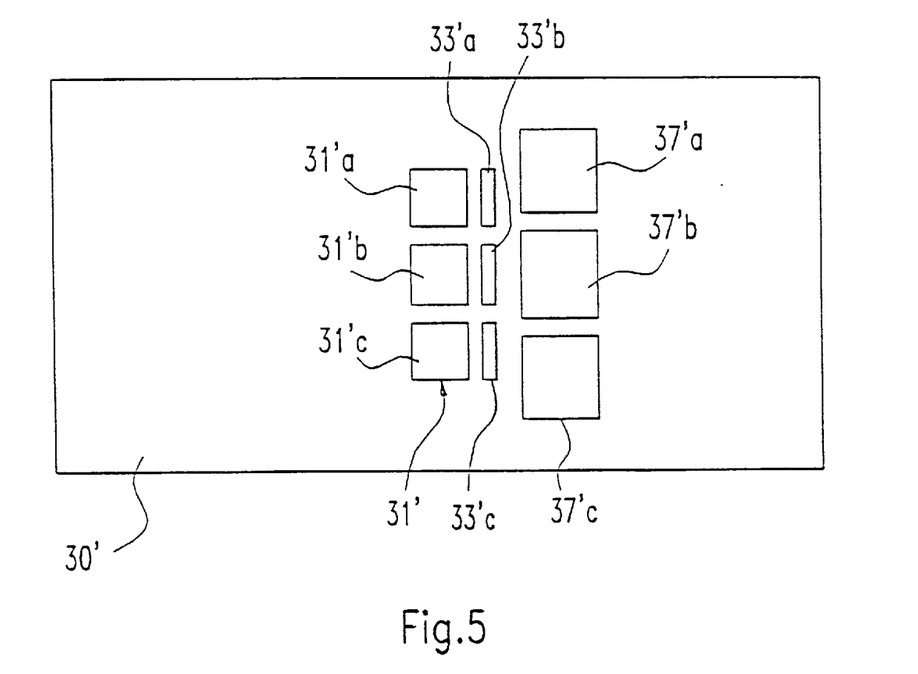
FIG. 5 is another view of an example of a sensor element.

The design of FIG. 5 has the disadvantage that because of the different field elements only deviations in the reflection plane itself can be recognized. This disadvantage is removed by the embodiment of FIG. 6.

Figure 6:
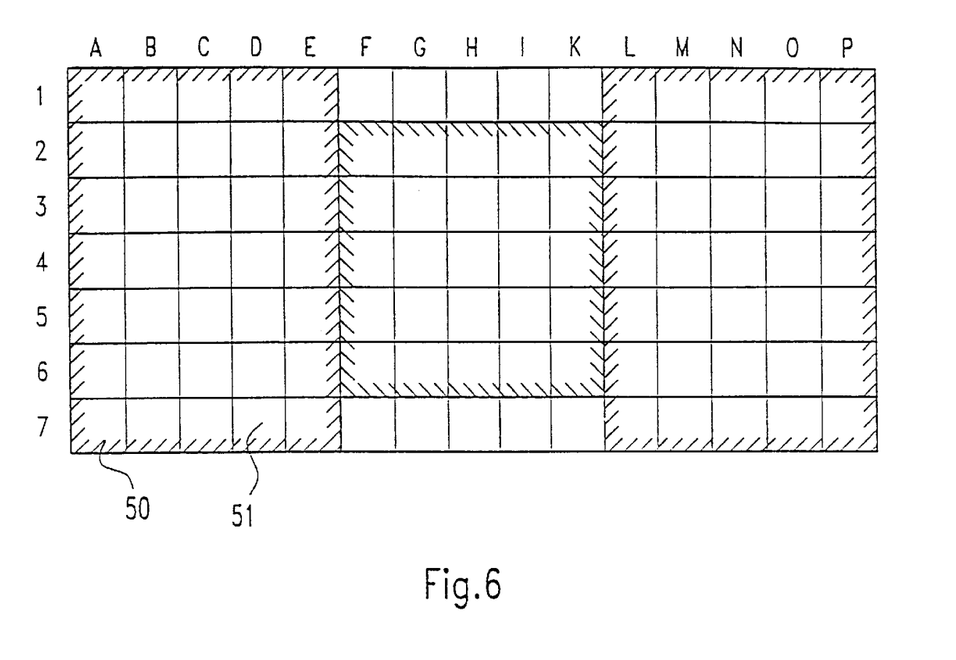
FIG. 6 is another embodiment of a sensor element in which the areas used for the light measurements may be varied.

In this embodiment a common substrate 50 is provided which is rectangularly designed and on which a plurality of light sensitive areas 51 is arranged, which in this embodiment have the form of a square. In the shown embodiment in the longitudinal dimension of the rectangle totally 15 field rows are provided which are labeled with the letters a to p, and in the dimension along the short edge length 7 fields are provided. The embodiment of this sensor preferably involves the charged coupled device technique (CCD).

The sensor is applied to a device as described with respect to FIG. 1.

For the function of the device switched such there are plural modifications:

A first modification of the function is constructed such as depicted in FIG. 6. In this embodiment a measurement is realized as illustrated with respect to FIGS. 2 and 3. There the individual areas are linked such that the intermediate area having the columns f, g, h, i, k and the rows 2, 3, 4, 5 and 6 are linked together such that they form a single area which corresponds to the light sensitive area 25 in the embodiment of FIG. 2. The columns a, b, c, d, e and the rows 1 to 7, the columns l, m, n, o, p and correspondingly the rows 1 to 7, respectively, are linked such, that they form a single light sensitive area which corresponds to the arrangement of the light sensitive areas 26, 27 of FIG. 2.

The measurement can be conducted in the same way as has been described with respect to the embodiment of FIGS. 2 and 3.

A very preferred alternative of the control method of the embodiment of FIG. 6 will now be described with respect to FIG. 7.

First it is to be noted that the division of the fields as has been described with respect to FIG. 6, wherein 15 columns and 7 rows have been formed, can be remarkably increased such that plural hundreds or thousands of columns and rows are available as measurement surfaces.

Figure 7:
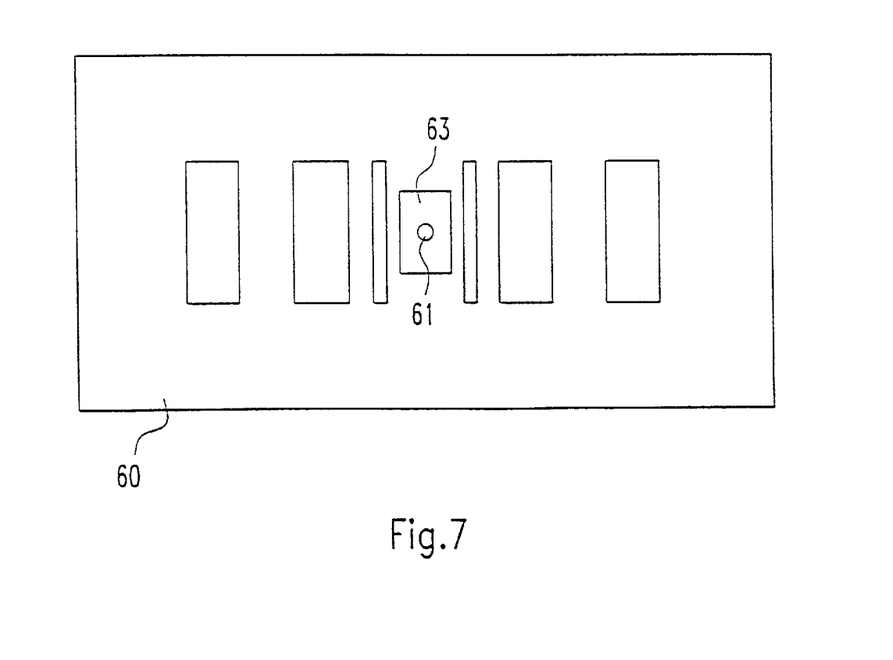
FIG. 7 is an illustration for further explanation of the embodiment of FIG. 6 in perspective view.

FIG. 7 shows a correspondingly arranged substrate 60, which is also rectangularly arranged and on which a plurality of such (not individually indicated) light sensitive areas is arranged, also here the CCD construction principle being used.

The control means can perform different measurement programs in this embodiment, the individual programs being stored in a memory and being able to be called via a corresponding input means, counter or the like by a user.

In a first alternative of the use of the sensor of FIG. 7 the individual light sensitive areas are switched by the control means such that measurement surfaces are created as depicted in FIG. 4, for example. In this alternative always the individual measurement surfaces or measurement points are used for the measurement, which lie within the predetermined field range, as indicated in FIG. 4 in the fields 31 to 37. The light which impinges onto the remaining light sensitive areas which are not arranged within such a measurement field are not taken into account in the measurement.

By this design it is possible to perform a reflection measurement according to different standards. If, for example a reflection measurement is performed according to standard ASTM 340, then the areas are added such as depicted in FIG. 4. If, however, only a single measurement is desired from which gloss and haze are to be detected, then the individual light sensitive areas are linked such that areas are created as depicted in FIG. 2. In this way by means of one sensor totally different measurement programs can be performed and simultaneously different reflection measurement standards may be realized.

In this alternative of the embodiment of FIG. 6 in the memory of the control means the field limits to be used for the respective measurement are fixed and stored and are not varied.

In a modification as shown in FIG. 7, the position of the individual fields with respect to each other is fixed, however the linked fields which constitute the light sensitive areas may be displaced on the sensor as a whole. In this procedure the control means determines in which individual field the light intensity is largest. In the embodiment of FIG. 7 this is indicated by a circle 61. It is assumed for the further measurement that the hitting point 61 marks the point which corresponds to the ideal reflection angle. Around the hitting point 61 a measurement area 63 is then realized by circuit means which corresponds to the measurement area 31 of FIG. 4 or the measurement area 25 of FIG. 2 and serves for measurement of gloss. The remaining measurement areas depicted in FIG. 7 correspond to measurement areas as depicted in FIG. 4. This alternative of the procedure exhibits the advantage that an exact adjustment of the sensor geometry with respect to the measurement surface is not necessary. The control means is able to take into account deviations of the measurement geometry and to correct them by itself. In this procedure it is possible to make the tolerances of the manufacture of the measurement device themselves larger, reducing the costs of the manufacture of the measurement device drastically. Moreover also changes of the measurement geometry occurring during use are automatically corrected such that means for adjustment of the individual elements of the measurement device are not necessary.

Figure 8:
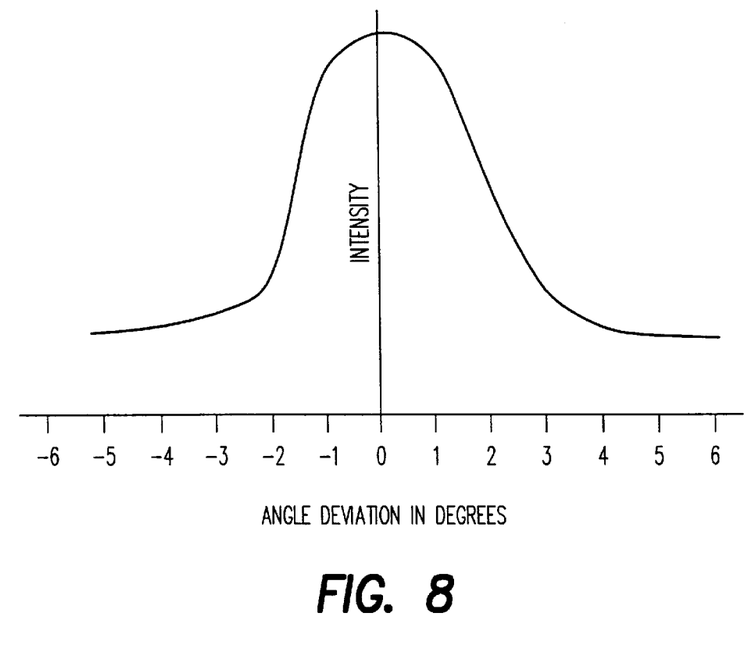
FIG. 8 is a diagram showing the reflection behavior of a surface, the ordinate being the measured light intensity and the abscissa being the angle deviation with respect to the ideal reflection angle.

An arrangement as has been shown in FIG. 6 and FIG. 7 further enables to record the reflection behavior on the surface in a broad range of reflection angles as has been shown with respect to FIG. 8.

In the diagram of FIG. 8 the ordinate is the measured light intensity, and the abscissa is the angle deviation with respect to the ideal reflection angle. The measured intensity is largest in the range of the ideal reflection angle and decreases with increasing angle distance. From the curve detected such the reflection behavior at the surface can be judged in a simple manner. Furthermore it is possible to deduce characteristic values from the curve which characterize the reflection behavior of surfaces according to the different standards. Thus, it is possible to record a measurement curve by performing a single measurement and to perform a following analysis numerically by the measurement device itself or in an external computing means, for example a PC.

The principal circuit arrangement of a measurement device as to be used in the embodiments of FIGS. 1 to 8 will now be described with respect to FIG. 9.

The principal measurement construction is identical for all embodiments shown, only the programming is different, depending on the sensor type used.

The measurement device comprises a control means 70 which includes a commercially available micro processor controlled by a program which is stored in a memory 71.

The communication of the control means 70 with the user is performed by an input means 72 which includes a number of switches to start the operation of the control means and to change between the individual operating modes (in the corresponding embodiments).

Besides the micro processor the control means includes input/output means which serve for the connection of the control means to the individual components of the device.

In order to activate and to perform the measurement the control means is connected to the light source 3 as well as to the sensor 14. The results of the measurement are shown in a display 75 which preferably is an LCD display. For the further analysis of the measurement a connection to an external computer 76 is provided.

The measurement device is supplied with current by a (not illustrated) battery.

The measurement device is preferably arranged in the housing 1 as a whole, which has the dimensions of a pocket book.

In order to avoid manufacturing dependent deviations of the single measurement devices, preferably each measurement device is individually calibrated. To this aim the measurement device is arranged on reference gloss tiles as provided by standard institutes, and the corresponding reflection characteristic values are measured. The corresponding values are then stored in the memory 71 and are durably available for conversion of the values measured by the sensor 14 into gloss characteristic values or the like.

Another embodiment of the invention will now be explained with respect to FIG. 10.

In this embodiment the device is arranged in a housing 100 as a whole which comprises an opening 101 to arrange the apparatus on the surface to be measured.

In contrast to the embodiments mentioned above, however, the apparatus is not directly applied to the surface, but by means of (schematically indicated) at least two rubber rolls 103, 104 or at least rubber wheels 103, 104, which are rotatably (not illustrated) supported in the housing 100. At least one of the rubber wheels or rolls is provided with a (not illustrated) distance measurement means for detecting angle movements of the rubber wheels 103 and outputting a representative electrical signal.

The device further comprises a light tubus 110 in which a point light source 111 is arranged. The tubus further comprises lens means 112 the characteristics of which will be discussed below.

The tubus 111 is arranged such that its optical axis is oriented in a predetermined angle (in the shown embodiment 45°) with respect to the surface 115 to be measured.

Moreover, the measurement tubus 120 is provided the optical axis of which is also oriented in a predetermined angle (from here also 45°) with respect to the surface 115 to be measured, said angle being identical to the angle in which the optical axis of the tubus 110 is oriented with respect to the surface, and both optical axis of both tubus crossing each other at the surface measurement point 115.

The measurement tubus 120 comprises a lens arrangement 121, an aperture means 122 and a measurement sensor 125 being perpendicularly arranged with respect to the optical axis.

Under an angle perpendicular to the surface measurement point 115 another illumination means 130 is provided in the upper portion of the housing, in which (in the embodiment) three illumination means are accommodated, namely three light-emitting diodes (LEDs), which exhibit different spectral characteristics, i. e. which irradiate light having different colors.

Figure 9:
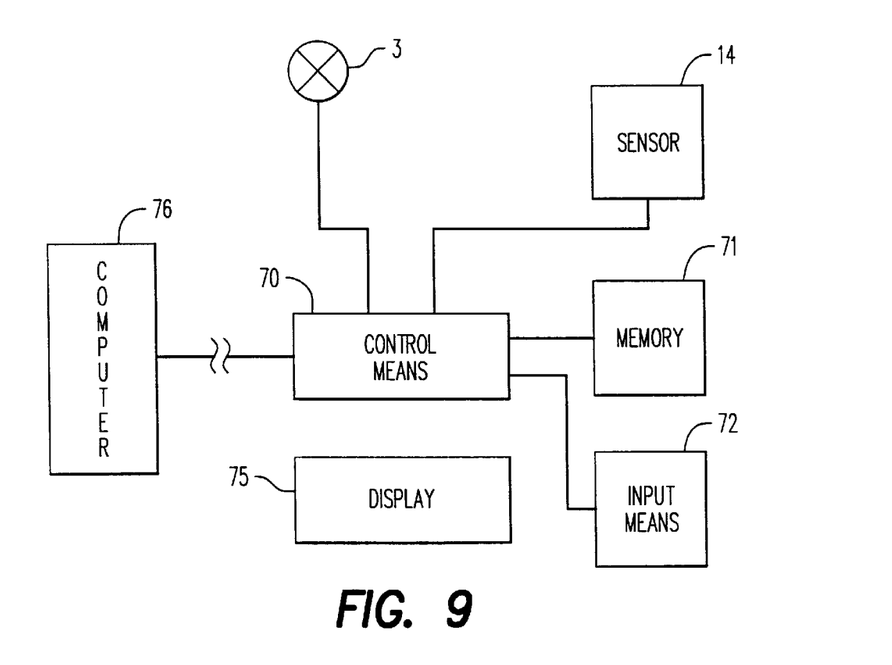
FIG. 9 shows the circuit design of a measurement device in principle used in the embodiments of FIGS. 1 to 8.

Moreover a (not illustrated) control means is provided having basically the construction of the control means of FIG. 9 and having switching means by use of which the user can choose between the different measurement procedures. Moreover, display means are provided to display the measurement result. Alternatively the device can be connected with a computer directly via a cable or wireless, preferably to a personal computer, in which the measurement results are detected and displayed and stored.

The function of this device is as follows:

The device is a universal device for measurement of visual characteristics of surfaces. In this case three measurements are principally possible:

1. the measurement of reflection characteristics as discussed with respect to the embodiments of FIGS. 1 to 9 of the present application;
2. the measurement of the color characteristics of the surface as described in the parallel application of the same applicant (attorney file 477P26, WO 96/09524) which has been filed at the same day as the present application with the German Patent Office and describes a color measurement device which is a further development of a color measurement device disclosed in DE 42 02 822 A1 (corresponding to U.S. Pat. No. 5,137,364), and
3. a method of quantified analysis of the physiological impression of reflection capable surfaces as disclosed in the WO 93/0433 corresponding to the European application 92916021 of the same applicant.

In the first measurement method, the reflection characteristics of the surface are measured as discussed with respect to FIGS. 1 to 9. In this measurement alternative, the light of the light source 111 is guided onto the surface in parallel ray direction and is received by the sensor means 125. The sensor means 125 in this universal measurement apparatus is a color CCD chip having a plurality of light sensitive areas being sensitive for three (or four) different wave length characteristics each. In the memory of the control means different measurement fields are stored as described with respect to FIG. 9 which are imaged by adding a plurality of these light sensitive points and enable the measurement of the reflection, the haze etc. Since in reflection measurements usually no color deviations are taken into account, the measurement results of the different color sensitive fields are added without specifying the measurement signal with respect to the color. Also another method alternative is possible such that the color characteristics of the reflected light can also be detected.

In this measurement alternative the light impinges onto the surface to be measured in parallel ray direction. This is achieved by the lens arrangement 112 which effects corresponding condensing of the light of the point light source 111.

Moreover all measurement possibilities are possible which have been discussed above with respect to FIGS. 1 to 9.

For color measurement the point light source 111 is turned off and means 130 is used as illumination means. This means includes three LEDs 132, 133, 134 which comprise different spectral characteristics and the light of which impinges onto the surface 115. From the surface the light is reflected and impinges into the measurement tubus 122 onto the sensor means 125. In the sensor means, the reflected signal is recorded, and in an analysis procedure as described in the references mentioned above or in the parallel application of the applicant, the spectral characteristics of the reflected light are determined. At this time the respective sensor areas having the same spectral characteristics are linked according to measurement fields such that the corresponding measurement areas have the effect of a sensor having a determined spectral characteristic. It is possible to provide different measurement fields such that also different reflection angles and the like may be determined.

It is important to note that the angle under which the light impinges onto the surface is selected such that no Fresnel reflection is measured. In this case the light of the LEDs irradiates perpendicularly with respect to the surface, and the measurement tubus is arranged under an angle of 45° with respect to the surface.

In the third measurement alternative which employs the measurement method shown in WO 93/04338 the device is manually moved across the surface to be measured. At this time the rubber wheels 103, 104 are rotating. The light source 111 is used as a point light source here.

For switching over the light source from the point light source to the light source having a parallel ray path there are different possibilities. The lens arrangement can be selected such that it can be pivoted out of the tubus. Moreover it is possible to move the lens arrangement of the light source with respect to each other along the optical axis of the tubus 110 so as to create different radiation patterns. For example, this can be achieved by providing the tubus 111 with two sleeves fitted into each other (not illustrated) and removable with respect to each other.

During the movement of the measurement apparatus across the surface the light irradiated from the point light source 111 is reflected by the surface and is detected by means of the measurement tubus and the sensor means 125. In this case the sensor means 125 is preferably adjusted such that only the light intensity is measured and that the spectral characteristics are not taken into account. Of course, it is also possible to take the spectral characteristics into account. During the movement the light intensity values of the sensor means 125 together with the distance measurement signals of the distance measurement means of the rubber wheel 103 are stored. After having passed a predetermined distance the reflection measurement values are analyzed as described in WO 93/04338, and based thereon the longer wavelength characteristics of the surface are measured (for example disturbances of a painture surface as orange peel and the like).

For the measurement of these values often means are used which occupy a total lab room. By means of the above described universal measurement apparatus the measurement of longer wavelength disturbances, the measurement of reflection characteristics of the surface with respect to gloss, haze and the like as well as the measurement of the color of the surface may be performed in a small manual apparatus.

In an alternative modification of the device plural measurement angles may be realized as it is known for reflection measurement apparatus in the state of the art. Thereby the light is directed under different angles to the surface such that also statements about the reflection behavior under different illumination angles are possible.

Moreover the change of the light source from the point light source to the parallel light source may also be achieved by providing two light tubus 110 which are spacially displaced with respect to each other, and simultaneously providing two light-receiving tubus having two sensor means 125.

Figure 10:
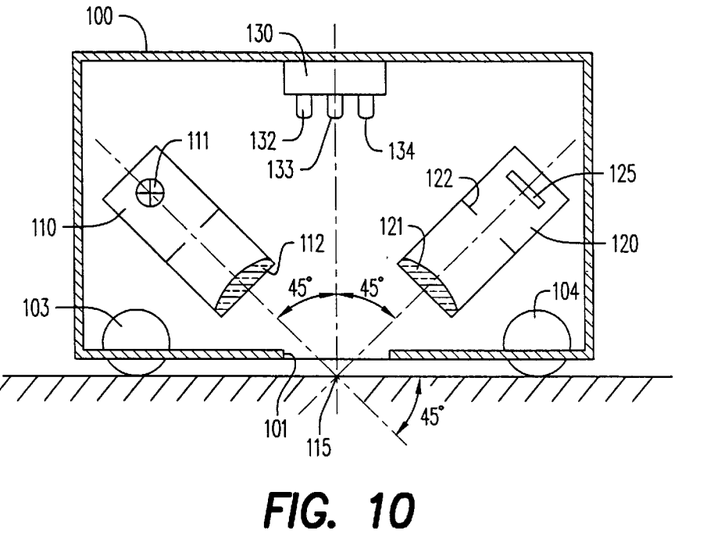
FIG. 10 is another embodiment of the present invention which is also suited for other measurements.

In the device shown in FIG. 10 three different measurement methods, the reflection measurement at a specified location of the surface, the reflection measurement at a larger sector of the surface and the color measurement are realized. As a modification of the shown embodiment also only two of these mentioned measurement principles may be realized. In a first modification these are the reflection measurement at a location of the surface and at a larger section of the surface. In this case the illumination means 130 may be omitted, and the sensor means 125 does not need to be arranged to recognize colors or different spectral characteristics of the reflected light. In this case the sensor means 125 can be arranged as depicted in FIGS. 2 to 7. In this case it is also possible to use a black white CCD chip.

In the second modification the device for measuring the reflection characteristics is provided at a predetermined location of the surface and also for color measurement. In this case the rubber wheels 103, 104 and the distance measurement means may be omitted. Furthermore, if the surface measurement is to be performed only under parallel ray direction, also the change over possibilities between point light source and light source having a parallel ray direction may be omitted.

In all shown embodiments the illumination is performed under a wavelength which is in the range 380 to 760 nm of visible light. The expression "light source" in the sense of the present application also includes radiation sources the radiation of which exhibits a longer or shorter wavelength.

I claim:

1. A device for measuring reflection characteristics of surfaces comprising:

a first optical means having a first light source for directing light irradiated from said first light source at a predetermined angle onto a surface to be measured;

a second optical means arranged at a predetermined angle with respect to said first optical means and for receiving light reflected from said surface to be measured, said second optical means comprising at least three photo sensors which are arranged such that each photo sensor measures an intensity of said reflected light in a range which corresponds to a different reflection angle, each photo sensor having a light sensitive area;

means for controlling said device and for detecting signals output by said at least three photo sensors, wherein said light sensitive areas of said at least three photo sensors are essentially arranged within a first plane and form an integrated device; said light sensitive areas being arranged on a common substrate and detecting said intensity of said reflected light essentially independently of each other; said light sensitive areas being arranged such that each light sensitive area detects said intensity of said reflected light within a predetermined angle range, wherein the light sensitive area of at least one of said at least three photo sensors is arranged that light reflected from an ideally reflecting surface impinges on said photo sensor, wherein the light sensitive areas of at least two of said at least three photo sensors have different dimensions.

2. The device according to claim 1, wherein said light sensitive areas are three light sensitive areas, a first essentially rectangular light sensitive area being arranged such that light rays reflected off an ideally reflecting surface symmetrically impinge onto said first light sensitive area, and second and third light sensitive areas each being provided at an opposite side of said first light sensitive area for receiving light rays the reflection angle of which is larger or smaller by a predetermined angle range than an angle at which light rays impinge onto said first light sensitive area when reflected off the ideally reflecting surface.

3. The device according to claim 1, wherein said light sensitive areas are directly located on said substrate.

4. The device according to claim 3, wherein said light sensitive areas are formed as individual stripes and said substrate is essentially rectangular, said stripes being arranged in said first plane with respect to their longitudinal extension, said first plane being essentially perpendicular to a second plane in which light rays are directed onto said surface to be measured and are reflected therefrom.

5. The device according to claim 3, wherein said plurality of light sensitive areas on said substrate are arranged such that a plurality of area elements are provided which are arranged in parallel columns and rows that are perpendicular to each other.

6. The device according to claim 5, wherein said light sensitive areas are essentially in the form of a square.

7. The device according to claim 1, wherein said light sensitive areas are symmetrically arranged with respect to a reference plane that runs through a point at which light rays impinge onto said surface to be measured and which is perpendicular to a plane in which light rays of said first optical means and light rays reflected from said surface to be measured are essentially located.

8. The device according to claim 1, wherein said substrate is designed essentially as a rectangle with respect to its extension in parallel to said light sensitive areas.

9. The device according to claim 5, wherein said plurality of area elements are connected to each other in charged coupled device technique.

10. The device according to claim 9, wherein said plurality of area elements comprise the same spectral characteristics for converting incident light into a black/white measurement.

11. The device according to claim 1, further comprising a third optical means for irradiating light having predetermined spectral characteristics and which is directed onto said surface to be measured under such an angle that light directly reflected according to a Fresnel reflection does not coincide with an angle under which said second optical means is directed onto said surface to be measured.

12. The device according to claim 11, wherein said third optical means includes a plurality of individual light emitting elements, said light emitting elements having different spectral characteristics with respect to each other.

13. The device according to claim 12, wherein said light emitting elements are designed with respect to their spectral characteristics that they at least partially overlap in a range of a wave length of visible light and are linearly independent from each other.

14. The device according to claim 1, wherein said device is relatively movable in a parallel direction to said surface to be measured, and further comprising distance measurement means for quantitatively detecting said parallel relative movement and memory means for storing reflection values measured along predetermined measurement locations on said surface to be measured and an associated relative position of said measurement locations.

15. The device according to claim 1, wherein said first optical means is arranged such that light is directed onto said surface to be measured with an essentially parallel ray path.

16. The device according to claim 1, wherein said first optical means is arranged such that said first light source acts as a point light source.

17. The device according to claim 1, further comprising at least two side areas, wherein said at least two side areas lie at a same angle distance range from a point at which light rays impinge onto a first light sensitive area when reflected off the ideally reflecting surface, and have the same dimensions.

18. A device for measuring reflection characteristics of surfaces comprising:

a first optical means having a first light source for directing light irradiated from said first light source at a predetermined angle onto a surface to be measured;

a second optical means arranged at a predetermined angle with respect to said first optical means and for receiving light reflected from said surface to be measured, said second optical means comprising a plurality of light sensitive area elements on a common substrate forming at least three photo sensors, each of said at least three photo sensors comprising a plurality of said light sensitive area elements;

means for controlling said device and for detecting signals output by said at least three photo sensors, said controlling means has a memory for storing specified area patterns and said light sensitive area elements are connected such that said specified area patterns correspond to a specified measurement area wherein said light sensitive area elements are arranged such that each has a light sensitive area that detects said intensity of said reflected light within a predetermined angle range;

wherein a plurality of said light sensitive area elements for each of said at least three photo sensors are connected according to a predetermined area pattern to form each of said at least three photo sensors;

wherein said at least three photo sensors measure the intensity of said reflected light essentially independently of each other.

19. The device according to claim 18, further comprising means for selecting a predetermined area pattern for a measurement.

20. The device according to claim 18, wherein said controlling means initially performs a measurement for determining on which light sensitive area element said intensity is largest, and wherein said area patterns are oriented with respect to a location of said light sensitive area elements having the highest light intensity.

21. The device according to claim 18, further comprising a third optical means irradiating light having predetermined spectral characteristics and which is directed onto said surface to be measured under such an angle that light directly reflected according to a Fresnel reflection does not coincide with an angle under which said second optical means is directed onto said surface to be measured.

22. The device according to claim 21, wherein said third optical means includes a plurality of individual light emitting elements, said light emitting elements having different spectral characteristics with respect to each other.

23. The device according to claim 22, wherein said light emitting elements are designed with respect to their spectral characteristics that said light emitting elements at least partially overlap in a range of a wave length of visible light and are linearly independent from each other.

24. The device according to claim 18, wherein said device is relatively movable in a parallel direction to said surface to be measured, and further comprising distance measurement means for quantitatively detecting said parallel relative movement and memory means for storing reflection values measured along predetermined measurement locations on said surface to be measured and an associated relative position of said measurement locations.

25. The device according to claim 18, wherein said first optical means is arranged such that light is directed onto said surface to be measured with an essentially parallel ray path.

26. The device according to claim 18, wherein said first optical means is arranged such that said first light source acts as a point light source.

27. The device according to claim 18, wherein said plurality of light sensitive areas are essentially in the form of a square.

28. The device according to claim 18, wherein said light sensitive area elements are symmetrically arranged with respect to a reference plane that runs through a point at which light rays impinge onto said surface to be measured and which is perpendicular to a plane in which light rays of said first optical means and light rays reflected from said surface to be measured are essentially located.

29. A device for measuring reflection characteristics of surfaces comprising:

a first optical means having a first light source for directing light irradiated from said first light source at a predetermined angle onto a surface to be measured;

a second optical means arranged at a predetermined angle with respect to said first optical means and for receiving light reflected from said surface to be measured, said second optical means comprising a plurality of light sensitive area elements on a common substrate, said light sensitive area elements being arranged to measure an intensity of said reflected light in ranges which correspond to different reflection angles;

means for controlling said device and for detecting signals output by said plurality of light sensitive area elements, wherein said plurality of light sensitive area elements are essentially arranged within a first plane that forms an integrated device, said light sensitive area elements being arranged on a common substrate and detecting said intensity of said reflected light essentially independently of each other, wherein said plurality of light sensitive areas on said substrate are arranged in parallel columns and rows which are perpendicular to each other, said light sensitive area elements being connected to each other in charged coupled device technique, and being designed such that at least three adjacent light sensitive area elements comprise different spectral characteristics such that a color of said reflected light is detectable by said area elements.

30. The device according to claim 29, wherein said plurality of light sensitive area elements are essentially in the form of a square.

31. The device according to claim 30, wherein said light sensitive area elements are symmetrically arranged with respect to a plane that runs through a point at which light rays impinge onto said surface to be measured and which is arranged perpendicular to a plane in which light rays of said first optical means and light rays reflected from said surface to be measured are essentially located.

32. The device according to claim 29, wherein said controlling means receives signals of said light sensitive area elements such that said intensity is measured on an area which is larger than an area of a single of said light sensitive area elements.

33. The device according to claim 32, wherein said controlling means has a memory for storing specified area patterns, and wherein said light sensitive area elements are connected such that said specified area patterns correspond to a specified measurement area.

34. The device according to claim 33, further comprising means for selecting a predetermined area pattern for a measurement.

35. The device according to claim 33, wherein said controlling means initially performs a measurement for determining on which light sensitive area element said intensity is largest, and said specified area patterns are oriented with respect to a location of said light sensitive area elements having the highest light intensity.

36. The device according to claim 29, further comprising a third optical means for irradiating light having predetermined spectral characteristics and which is directed onto said surface to be measured under such an angle that light directly reflected according to a Fresnel reflection does not coincide with an angle under which said second optical means is directed onto said surface to be measured.

37. The device according to claim 36, wherein said third optical means includes a plurality of individual light emitting elements, said light emitting elements having different spectral characteristics with respect to each other.

38. The device according to claim 37, wherein said light emitting elements are designed with respect to their spectral characteristics that said light emitting elements at least partially overlap in a range of a wave length of visible light and are linearly independent from each other.

39. The device according to claim 29, wherein said device is relatively movable in a parallel direction to said surface to be measured, and further comprising distance measurement means for quantitatively detecting said parallel relative movement and memory means for storing reflection values measured along predetermined measurement locations on said surface to be measured and an associated relative position of said measurement locations.

40. The device according to claim 29, wherein said first optical means is arranged such that light is directed onto said surface to be measured with an essentially parallel ray path.

41. The device according to claim 29, wherein said first optical means is arranged such that said first light source acts as a point light source.

42. A method of measuring visual characteristics of surfaces comprising:
    providing first optical means with a light source to direct light at a predetermined angle onto a surface to be measured, and
    providing second optical means, which includes a sensor means having a plurality of light sensitive areas, for detecting light reflected from said surface to be measured; and
    providing control means for controlling said device and for detecting signals output from said sensor means,
    providing memory means for storing program instructions for instructing said control means,
    wherein said memory means stores at least one predetermined measurement geometry in accordance to which said plurality of individual light sensitive areas are connected to a common measurement area such that the intensity of light impinging onto said plurality of said individual light sensitive areas is detected as a common value,
    wherein measuring is performed such that said surface to be measured is irradiated with said light source and that said output signals of said sensor means measured for said at least one predetermined measurement geometry are detected.

43. The method according to claim 42, wherein said memory means has a plurality of measurement geometries stored therein, and further comprising switching means for selecting one of said at least one measurement geometry.

44. The method according to claim 42, wherein at least three adjacent light sensitive areas comprise a different spectral characteristic and are connected such that spectral characteristics and particularly a color of said reflected light is detectable therewith.

* * * * *